United States Patent
Tong et al.

(10) Patent No.: US 8,637,092 B2
(45) Date of Patent: Jan. 28, 2014

(54) PHARMACEUTICAL COMPOSITION FOR TREATING DIABETES AND ITS PROCESS FOR PREPARATION

(75) Inventors: Xiaolin Tong, Tianjin (CN); Yonghong Zhu, Tianjin (CN); Shuiping Zhou, Tianjin (CN); Xiuhui E, Tianjin (CN); Shuangming Wang, Tianjin (CN); Zhongting Xia, Tianjin (CN)

(73) Assignee: Tasly Pharmaceutical Group Co., Ltd., Tianjin (CN)

( * ) Notice: Subject to any disclaimer, the term of this patent is extended or adjusted under 35 U.S.C. 154(b) by 699 days.

(21) Appl. No.: 12/601,236

(22) PCT Filed: Jul. 28, 2008

(86) PCT No.: PCT/CN2008/001383
§ 371 (c)(1),
(2), (4) Date: Dec. 10, 2009

(87) PCT Pub. No.: WO2009/015557
PCT Pub. Date: Feb. 5, 2009

(65) Prior Publication Data
US 2010/0136150 A1    Jun. 3, 2010

(30) Foreign Application Priority Data

Aug. 2, 2007  (CN) .......................... 2007 1 0058571
Aug. 2, 2007  (CN) .......................... 2007 1 0058572
Aug. 2, 2007  (CN) .......................... 2007 1 0058573
Aug. 2, 2007  (CN) .......................... 2007 1 0058574

(51) Int. Cl.
*A61K 36/00* (2006.01)
*A61K 36/752* (2006.01)
*A61K 36/539* (2006.01)
*A61K 36/42* (2006.01)

(52) U.S. Cl.
USPC ........... 424/725; 424/735; 424/736; 424/741; 424/758; 424/773; 424/778

(58) Field of Classification Search
None
See application file for complete search history.

(56) References Cited

U.S. PATENT DOCUMENTS 7,122,214 B2  10/2006  Xie

FOREIGN PATENT DOCUMENTS

| CN | 1725929 A | * | 1/2006 |
| CN | 1726929 A | | 2/2006 |
| JP | 2004-521883 | | 7/2004 |
| JP | 2004-522952 | | 7/2004 |
| JP | 2005-539006 | | 12/2005 |
| WO | 02/058625 | | 8/2002 |
| WO | 2004/012651 | | 12/2004 |

OTHER PUBLICATIONS

XP002588200, Database WPI Week 200655, Thomson Scientific, London, GB; AN 2006-530161.
Capital Medicine, 24(7), Clinical Practice from Shi Jinmo, p. 17-36 (Jul. 2005).
China's Naturopathy, (1), Gong Xiangjun, Therapeutical Development in Diabetees by TCM, p. 63-65 (Jan. 1998).
Tang, Wang K., "Zheng Zhi Zhun Sheng: Xiaodan" (English Translation "Diabetes"), 1998.
Office action dated Sep. 28, 2012 from the corresponding Australian application, Application No. 2008281227 (3 pages).
European Supplementary Search Report completed on Jun. 22, 2010 and mailed Jun. 30, 2010, EPO Application No. 08783574.
XP002588200, Database WPI Week 200655, Thomson Scientific, London, GB; AN 2006-530161, Feb. 1, 2006.

* cited by examiner

*Primary Examiner* — Chris R Tate
*Assistant Examiner* — Deborah Davis
(74) *Attorney, Agent, or Firm* — Ladas & Parry, LLP

(57) ABSTRACT

The present invention relates to methods for preparing a pharmaceutical composition for treating diabetes mellitus and the pharmaceutical composition prepared by the methods. The pharmaceutical composition of the present invention comprises extracts of the following crude drugs: 5-40 weight parts of *Radix Trichosanthis* (Tianhuafen), 10-30 weight parts of *Radix Bupleuri* (Chaihu), 3-15 weight parts of *Fructus Aurantii Immaturus* (Zhishi), 1-6 weight parts of *Radix et Rhizoma Rhei* (Dahuang), 1-12 weight parts of *Rhizoma Pinelliae* (Banxia), 3-15 weight parts of *Radix Scutellariae* (Huangqin), 1-12 weight parts of *Rhizoma Coptidis* (Huanglian), 3-15 weight parts of *Radix Paeoniae Alba* (Baishao) and 5-20 weight parts of *Fructus Mume* (Wumei), and optionally comprises pharmaceutically acceptable excipient. Also, the pharmaceutical composition of the present invention can further comprise *Fructus Crataegi* (Shanzha). Additionally, the present invention discloses four methods for preparing the pharmaceutical composition.

26 Claims, No Drawings

PHARMACEUTICAL COMPOSITION FOR TREATING DIABETES AND ITS PROCESS FOR PREPARATION

CROSS-REFERENCE TO RELATED APPLICATIONS

This application is the U.S. National Stage of International Patent Application No. PCT/CN2008/001383, filed on Jul. 28, 2008, which claims priority to Chinese Patent Application Nos. 200710058571.0, 200710058572.5, 200710058573.X, and 200710058574.4, all filed on Aug. 2, 2007, the disclosures of which are incorporated herein by reference.

FIELD OF THE INVENTION

The present invention relates to four methods for preparing a pharmaceutical composition for treating diabetes mellitus (also referred to as diabetes) and the pharmaceutical composition prepared by the methods.

BACKGROUND OF THE INVENTION

Diabetes mellitus (DM) is a chronic progressive lifelong disease, which is caused by body's metabolic disorder of carbohydrate, protein and lipid with characteristical manifestations of hyperglycemia and glycosuria. It can lead to complications of heart and kidney, blindness and even amputation. Recently, clinical studies showed that morbidity of DM has been rising year by year. By now, the number of patient with DM has amounted to 1.5-hundred millions all over the world. In China, the number of patient with DM has been over 40 millions. In DM cases, most of the patients belong to non-insulin-dependent diabetes mellitus (NIDDM, Type II), and a little belong to insulin-dependent DM (Type I). Thus, most of DM patients need medicine lifelong.

Now, treatment for DM is still dominated by chemical drugs, such as the sulfonamides, biguanide drugs, glucosidase inhibitor, glinides and insulin sensitizer etc. However, long-term use of these drugs will bring about severe side effects.

Traditional Chinese medicine (TCM) has a long history in prevention and treatment of DM. After thousand years of practice, much precious experience has been accumulated and the unique academic system has been established. A lot of glucose-reducing TCMs have been recorded in the TCM classics, for example *Rhizoma Alismatis* (Zexie), *Rhizoma Anemarrhenae* (Zhimu), *Radix panacis quinquefolii* (Xiyangshen), *Radix Puerariae Lobatae* (Gegen), *Radix Rehmanniae* (Dihuang) and pollen grain (Huafen) etc. Traditionally, treating DM by TCM is based on clinical symptoms according to "Sanxiao" theory, but has no good therapeutic method in the stage of impaired-glucose-tolerance and early stage of DM.

The main cause of DM is liver and stomach, and the existence of gloomy heat in body is the pathogenesis basis for "Xiaoke" disease (TCM name of DM). In light of the TCM theory of relieving liver depression and removing spleen dampness, it is necessary to adopt the method of regulation as the primary measurement, which is considered as a therapeutic way aiming at pathogenesis. Tangminling (the Chinese name of the pharmaceutical composition of the present invention) acts as relieving stagnancy to clear away stomach-heat, nourishing Yin to remove fire and dredging Fu to purge turbidity. It addresses both the symptoms and root cause. Since the gloomy heat has been eliminated, Qi and Yin will be recovered automatically. As elaborated in Xiaodan fascicule of Zheng Zhi Zhun Sheng (a great work written by Wang Ken Tang in Ming dynasty), an open way and vigorous body fluid could render Qi and blood suited for each other, and disease self-recovered. Accordingly, the therapeutic method of DM is to relieve stagnancy to clear away stomach-heat, nourish Yin to remove fire and dredge Fu to purge turbidity.

According to traditional TCM theory, the gastrointestinal stagnancy caused by overeating and reduced exercise usually checks transportation of Qi in "Zhongjiao" (middle warmer), which results in the closedown of dredging function of liver and gall. Stasis is converted into heat, the heat of "Sanjiao" (triple warmer) present in the organs of liver, gall, stomach, intestine and lung. Therefore, *Rhizoma Coptidis* and *Radix et Rhizoma Rhei* are used as the monarch drug, in which the *Rhizoma Coptidis* plays a part of clearing up stomach heat and *Radix et Rhizoma Rhei* dredging intestinal heat based on the theory of treating sweet by bitter. *Radix Paeoniae Alba*, *Radix Scutellariae* and *Radix Bupleuri* are used as the minister drug, where the *Radix Paeoniae Alba* plays a part of nourishing liver and astringing Yin, assisting the monarch drugs to clear up the heat in "Sanjiao" without damaging Yin; the *Radix Bupleuri* going into Shaoyang gall meridian and Jueyin liver meridian to clear up the heat of liver and gall and dredging spleen and stomach; the *Radix Scutellariae* clearing up the heat of lung and liver. The *Fructus Aurantii Immaturus* and raw *Fructus Crataegi* act as regulating Qi, digesting food and dispersing stasis, working with the *Radix et Rhizoma Rhei* to facilitate stomach and intestine; the *Rhizoma Pinelliae* with the *Rhizoma Coptidis* to render acrid opening and bitter downbearing to open middle warmer. Therefore, all of three drugs are used as assistant drug. The *Fructus Mume* acts as astringing Yin to regenerate body fluid based on the theory of treating sweet by acidity, working with the *Radix Trichosanthis* to make stomach's Yin vigorous. So it should be called as guide drug.

Based on the TCM theory of Gloomy Heat, a pharmaceutical composition has been found, which is composed of *Radix Trichosanthis* (Tianhuafen), *Radix Bupleuri* (Chaihu), *Fructus Aurantii Immaturus* (Zhishi), *Radix et Rhizoma Rhei* (Dahuang), *Rhizoma Pinelliae* (Banxia), *Radix Scutellariae* (Huangqin), *Rhizoma Coptidis* (Huanglian), *Radix Paeoniae Alba* (Baishao) and *Fructus Mume* (Wumei) etc. It has a better efficacy on treating DM. The composition has been disclosed in an early Chinese patent application by the applicant (No. 200410020220.7). However, the method used was based on the traditional ethanol-extraction method. Due to limitations in chemical property of solvent, a large amount of water-soluble active components are lost in the extract obtained by this method. Both the yields and the contents of the active components of the extract are low. Thus, the administration dosage is high, and consequently the side-effects are increased correspondingly.

SUMMARY OF THE INVENTION

The objective of the present invention is to provide a pharmaceutical composition for treating DM with the following quantitative formula. The pharmaceutical composition is prepared by the methods described below, which can solve the above-mentioned problems in prior arts.

Another objective of the present invention is to provide methods for preparing a pharmaceutical composition for treating DM and the pharmaceutical composition prepared by the methods. The pharmaceutical composition of the present invention comprises extracts of the following crude drugs by weight part: 5-40 weight parts of *Radix Trichosanthis*, 10-30 weight parts of *Radix Bupleuri*, 3-15 weight parts of *Fructus Aurantii Immaturus*, 1-6 weight parts of *Radix et Rhizoma*

*Rhei*, 1-12 weight parts of *Rhizoma Pinelliae*, 3-15 weight parts of *Radix Scutellariae*, 1-12 weight parts of *Rhizoma Coptidis*, 3-15 weight parts of *Radix Paeoniae Alba* and 5-20 weight parts of *Fructus Mume*, and optionally comprises pharmaceutically acceptable excipient. The pharmaceutical composition can be prepared by any one of the following four methods.

The first method comprises the following steps:
a. providing the crude drugs in accordance with the weight parts as described above;
b. extracting the crude drugs with water by reflux, filtering the extract liquid and concentrating under reduced pressure;
c. adding ethanol into the concentrated extract liquid to make the ethanol content to 65-75% and filtering;
d. concentrating the filtrate under reduced pressure to produce an extract;
e. optionally adding excipient into the extract of step (d) to prepare into pharmaceutically acceptable dosage form.

The second method comprises the following steps:
a. providing the crude drugs in accordance with weight parts as described above;
b. extracting the crude drugs with water by reflux, cooling down the extract liquid, filtering and combining to give a filtrate;
c. loading the filtrate onto macro-porous adsorption resin, washing with water, discarding the eluate, continuing to wash with ethanol having a certain concentration, combining the ethanol eluate and recovering ethanol under reduced pressure to give an extract;
d. optionally adding excipient into the extract of step (c) to prepare into pharmaceutically acceptable dosage form.

The third method comprises the following steps:
a. providing the crude drugs in accordance with weight parts as described above;
b. extracting the following crude drugs with ethanol having a certain concentration by reflux: *Radix Bupleuri*, *Radix Paeoniae Alba*, *Fructus Aurantii Immaturus*, *Radix et Rhizoma Rhei*, *Radix Scutellariae* and *Rhizoma Coptidis*, cooling down the extract liquid, filtering and combining;
c. adding the other drugs into the drug residue of step (b), continuously extracting with water by reflux, concentrating the extract liquid under reduced pressure, followed by adding ethanol into the concentrated extract liquid to make the ethanol content to 65-75% and filtering;
d. combining the filtrate of steps (b) and (c) and concentrating into an extract;
e. optionally adding excipient into the extract of step (d) to prepare into pharmaceutically acceptable dosage form.

The fourth method comprises the following steps:
a. providing the crude drugs in accordance with weight parts as described above;
b. extracting the *Radix Scutellariae* with water by reflux, combining the extract liquid, adjusting pH value to 1.5-2.0, keeping temperature, standing still, filtering, washing the sediments with water until the pH value becomes 5-6, drying to give the dry powder of *Radix Scutellariae* extract;
c. extracting the *Rhizoma Coptidis* with ethanol by reflux, combining the extract liquid, filtering, recovering ethanol until no flavor of ethanol can be smelled, adjusting the pH value to 1-2, storing under a cold condition overnight, filtering, washing the sediments with water until the pH value becomes 5-6, drying to give the dry powder of *Rhizoma Coptidis* extract;
d. extracting the other drugs with water by reflux, combining the extract liquid, concentrating, cooling down, followed by adding 95% ethanol to make the ethanol content to 70%, standing still, filtering, recovering ethanol to give an extract, drying to give the dry powder of extract, and;
e. combining well the dry powder of extracts obtained in the above three steps, into which excipient is added optionally to prepare into pharmaceutically acceptable dosage form.

According to one embodiment of the present invention, the composition prepared by the methods of the present invention preferably comprises the following crude drugs: 9 weight parts of *Radix Trichosanthis*, 12 weight parts of *Radix Bupleuri*, 9 weight parts of *Fructus Aurantii Immaturus*, 3 weight parts of *Radix et Rhizoma Rhei*, 6 weight parts of *Rhizoma Pinelliae*, 9 weight parts of *Radix Scutellariae*, 6 weight parts of *Rhizoma Coptidis*, 9 weight parts of *Radix Paeoniae Alba* and 9 weight parts of *Fructus Mume*.

On the basis of the formulation above, *Fructus Crataegi* (Shanzha) can be added into the formulation of the pharmaceutical composition. The reasons are as follows: *Fructus Crataegi* acidifies sweetness and nourishes Yin, not only prevent excessive damage to Yin caused by the dissipation of acridity, but also achieve the purpose of inhibiting sweetness by sour and bitterness. It showed a good effect of dispersing gloomy and clearing up heat when combining with the other crude drugs. Thus, the pharmaceutical composition preferably comprises the following crude drugs: 5-40 weight parts of *Radix Trichosanthis*, 10-30 weight parts of *Radix Bupleuri*, 3-15 weight parts of *Fructus Aurantii Immaturus*, 1-6 weight parts of *Radix et Rhizoma Rhei*, 1-12 weight parts of *Rhizoma Pinelliae*, 3-15 weight parts of *Radix Scutellariae*, 1-12 weight parts of *Rhizoma Coptidis*, 3-15 weight parts of *Radix Paeoniae Alba*, 5-20 weight parts of *Fructus Mume* and 3-15 weight parts of *Fructus Crataegi*.

More preferably, the pharmaceutical composition of the present invention comprises following crude drugs by weight part: 10-30 weight parts of *Radix Trichosanthis*, 10-30 weight parts of *Radix Bupleuri*, 3-15 weight parts of *Fructus Aurantii Immaturus*, 1-6 weight parts of *Radix et Rhizoma Rhei*, 1-12 weight parts of *Rhizoma Pinelliae*, 3-15 weight parts of *Radix Scutellariae*, 1-12 weight parts of *Rhizoma Coptidis*, 3-15 weight parts of *Radix Paeoniae Alba*, 5-20 weight parts of *Fructus Mume* and 3-15 weight parts of *Fructus Crataegi*.

Mostly preferably, the pharmaceutical composition of the present invention comprises following crude drugs: 30 weight parts of *Radix Trichosanthis*, 12 weight parts of *Radix Bupleuri*, 9 weight parts of *Fructus Aurantii Immaturus*, 3 weight parts of *Radix et Rhizoma Rhei*, 6 weight parts of *Rhizoma Pinelliae*, 9 weight parts of *Radix Scutellariae*, 6 weight parts of *Rhizoma Coptidis*, 9 weight parts of *Radix Paeoniae Alba*, 15 weight parts of *Fructus Mume* and 9 weight parts of *Fructus Crataegi*, or the pharmaceutical composition of the present invention comprises following crude drugs by weight part: 15 weight parts of *Radix Trichosanthis*, 12 weight parts of *Radix Bupleuri*, 9 weight parts of *Fructus Aurantii Immaturus*, 3 weight parts of *Radix et Rhizoma Rhei*, 6 weight parts of *Rhizoma Pinelliae*, 9 weight parts of *Radix Scutellariae*, 6 weight parts of *Rhizoma Coptidis*, 9 weight parts of *Radix Paeoniae Alba*, 15 weight parts of *Fructus Mume* and 9 weight parts of *Fructus Crataegi*.

Specifically, in the first method of the present invention, the following steps are preferable:
a) In the step (b), the extraction-by-reflux is preferably performed twice with water of 10 times (×10 fold) the weight of the crude drugs for 1.5 hour per time. Preferably, the extract liquid is concentrated into a concentrated extract liquid with the final volume (L) to the initial weight of the crude drugs (kg) in ratio of 1:1;

b) In the step (c), the concentration of the added ethanol preferably is 90-100%, more preferably 95%. After adding ethanol, the concentrated extract liquid contains 70% ethanol.

Due to using the above method of water-extraction and ethanol-precipitation, in the pharmaceutical composition prepared by the method, the content of the active components significantly increased and the content impurities are remarkably decreased. Hence, the administration dosage is decreased.

In the second method of the present invention, the following steps are preferable:

1. In the step (b), the extraction-by-reflux is preferably performed twice with water of 10 times (×10 fold) the weight of the crude drugs for 1.0 hour per time.

2. In the step (c), the macro-porous resin preferably is AB-8 type; the weight ratio of the resin to the crude drugs preferably is 1:1.5-1:3, more preferably 1:2. The extract liquid is loaded preferably in a speed of 4-6 times the column volume per hour. The amount of the water for washing preferably is 4-6 times the column volume. The concentration of ethanol for washing preferably is 80-95%, more preferably 90%; the volume of ethanol for washing preferably is 2-5 times the column volume. The ethanol is recovered under reduced pressure preferably at a temperature of 60-80° C. By recovering ethanol under reduced pressure, an extract is obtained with a relative density of 1.25-1.35, preferably 1.30.

Water-extraction is adopted in the above method, ensuring water-soluble active components such as saikosaponin, berberin(berberine hydrochloride), baicalin, chrysophanol, paeoniflorin and synephrine etc., can be extracted from the crude drug to a greatest extent. In the present method, many efficient extraction steps are used, including macro-porous resin adsorption and washing by water to remove impurities, and eluting active components with ethanol aqueous solution. By these means, the majority of impurities can be removed and the active components can be retained.

The pharmaceutical composition prepared by the above method is characteristic of remarkably increased contents of the active components and greatly decreased contents of impurities, and the administration dosage is decreased correspondingly. Meanwhile, the stability between batches is ensured.

In the third method of the present invention, the following steps are preferable:

1. In the step (b), the concentration of the ethanol is 75-90%, preferably 80%; and preferably, the extraction-by-reflux is performed twice with ethanol of 10 times the weight of the crude drugs of the step (b) for 1.5 hour per time.

2. In the step (c), the extraction-by-reflux preferably is performed twice with water of 10 times the weight of the total weight of the crude drugs of the step (c) and the drug residue of step (b) for 1.5 hour per time; the extract liquid is preferably concentrated into a concentrated extract liquid with the final volume (L) to the initial weight of the crude drugs (kg) in ratio of 1:1. The concentration of the added ethanol preferably is 90-100%, more preferably 95%; after adding ethanol, the concentrated extract liquid contains 65-75%, preferably 70% ethanol.

In the above method, six crude drugs of *Radix Bupleuri, Radix Paeoniae Alba, Fructus Aurantii Immaturus, Radix et Rhizoma Rhei, Radix Scutellariae* and *Rhizoma Coptidis* are extracted with ethanol firstly, then the obtained residues are combined with the other crude drugs and extracted with water. This ensures that the active components in the six crude drugs can be fully extracted. While the other drugs are extracted only by water to obtain their water-soluble components because all active components in these crude drugs are considered to be water-soluble. In the composition prepared by the above method, the content of the active components significantly increased and the content of impurities are remarkably decreased. Hence, the administration dosage is decreased.

In the fourth method of the present invention, the following steps are preferable:

1. In the step (b), the extraction-by-reflux is performed twice with water of 10 times the weight of the *Radix Scutellariae* for 1 hour per time; the extract liquid is preferably kept at 75-85° C., more preferably at 80° C.

2. In the step (c), the extraction-by-reflux is preferably performed twice with ethanol of 10 times the weight of the *Rhizoma Coptidis* for 2 hours per time; the concentration of ethanol preferably is 70-85%, more preferably 75%.

In the step (b) and step (c), the pH is preferably adjusted by concentrated hydrochloride acid.

3. In the step (d), the extraction-by-reflux is preferably performed twice with water of 10 times the weight of the other crude drugs for 1 hour per time; the combined extract liquid is concentrated into a concentrated extract liquid with a relative density of 1.03-1.07, preferably 1.05; after adding ethanol, recovering ethanol to give an extract preferably with a relative density of 1.25-1.35, more preferably 1.30.

In the present method, the *Radix Scutellariae, Rhizoma Coptidis* and the other crude drugs are extracted respectively. The water extraction or ethanol extraction is selected according to their different chemical properties, and then pH value is adjusted. In the pharmaceutical composition prepared by the above method, the content of the active components significantly increased and the content of impurities are remarkably decreased. Hence, the administration dosage is decreased.

According to the above methods of the present invention, a pharmaceutical composition having the above formulation for treatment of diabetes mellitus can be prepared. The composition of the present invention can be prepared by conventional method into any one of conventional dosage forms with conventionally used excipients known in prior arts. For example, the above crude drugs can be administrated in many manners: being powdered and infused with water; being prepared into an extract, dried, pulverized, sifted, powdered and infused with water, or the obtained extract being prepared into tablet or capsule and administrated orally, or the obtained extract being prepared into injection etc. To the skilled in the arts, however, these are not intended to limit the scope of the present invention.

The pharmaceutical composition prepared by the method of the present invention has the function of lowering blood sugar, having a good effect of treating DM clinically.

Herein, when the concentration of ethanol or the content of ethanol (the content of ethanol in the system) is expressed by percentage, it refers to volume percentage except where otherwise noted.

THE DETAILED DESCRIPTION OF THE INVENTION

The following preparative and experimental examples are provided for purposes of further illustration only and are not intended to limit the scope of the invention in any way.

EXAMPLE 1

Formulation: 750 g of *Radix Trichosanthis*, 1500 g of *Radix Bupleuri*, 450 g of *Fructus Aurantii Immaturus*, 150 g of *Radix et Rhizoma Rhei*, 150 g of *Rhizoma Pinelliae*, 450 g of *Radix Scutellariae*, 150 g of *Rhizoma Coptidis*, 450 g of *Radix Paeoniae Alba* and 750 g of *Fructus Mume*.

The composition is prepared by the following method:

The above nine crude drugs are extracted twice by reflux with water of 10 times the weight of the crude drugs, 1.5 hour per time. The extract liquid is filtered, concentrated under reduced pressure into a concentrated extract liquid with the final volume (L) to the initial weight of the crude drugs (kg) in ratio of 1:1, 90% ethanol is added to make the content of ethanol to 65%. Obtained extract liquid is filtered and concentrated under reduced pressure into a dense extract.

EXAMPLE 2

Identical formulation with that of the Example 1 is provided.

The composition is prepared by the following method:

The following six crude drugs (*Radix Bupleuri, Radix Paeoniae Alba, Fructus Aurantii Immaturus, Radix et Rhizoma Rhei, Radix Scutellariae* and *Rhizoma Coptidis*) are extracted twice by reflux with 75% ethanol of 10 times the weight of the crude drugs for 1.5 hour per time to give the extract liquid (1) and the drug residue. The extract liquid (1) is filtered for further use.

Adding *Radix Trichosanthis, Fructus Mume* and *Rhizoma Pinelliae* into the drug residue, the extraction-by-reflux is performed twice with water of 10 times the total weight of the three crude drugs and the drug residue for 1.5 hour per time to give extract liquid (2). The extract liquid (2) is concentrated into a concentrated extract liquid with the final volume (L) to the initial weight of the crude drugs (kg) in ratio of 1:1. 90% ethanol is added to make the content of ethanol to 65%, filtering for further use.

Combining the above extract liquid, and concentrating under reduced pressure into a dense extract.

EXAMPLE 3

Identical formulation with that of the Example 1 is provided.

The composition is prepared by the following method:

The above nine crude drugs are extracted twice by reflux with water, adding 48.5 kg water in each one-hour extraction; cooling down the extract liquid, filtering and combining. The combined filtrate is loaded onto 3.2 kg of AB-8 type macroporous adsorption resin in a speed of 4 times the column volume per hour. After washing with water of 4 times the column volume, the eluate is discarded. Then, the washing is conducted again with 80% ethanol of 2 times the column volume, and the ethanol eluate is combined. The ethanol is recovered from the combined ethanol eluate at 80° C. under reduced pressure to give an extract with a relative density of 1.25. Vacuum-dried is performed at 70° C. to obtain a dry extract, which is pulverized and screened through 80-mesh sieve. Lactose is added into the screened dry powder to prepare into capsules.

EXAMPLE 4

Identical formulation with that of the Example 1 is provided.

The composition is prepared by the following method:

Extracting twice by reflux the *Radix Scutellariae* with water of 10 times the weight of the *Radix Scutellariae* for 1 hour per time; combining the extract liquid, adjusting pH value with concentrated hydrochloride acid to 1.5-2.0; the extract liquid is kept at 75° C. for 1 hour, standing still, filtering, washing the sediments with water until the pH value becomes 5-6, drying, pulverizing the obtained dry extract and screening through 80-mesh sieve to give the extract of *Radix Scutellariae*.

Extracting twice by reflux the *Rhizoma Coptidis* with 70% ethanol of 10 times the weight of the *Rhizoma Coptidis* for 2 hours per time; combining the extract liquid, filtering, recovering ethanol until no flavor of ethanol can be smelled, adjusting the pH value with concentrated hydrochloride acid to 1-2, storing under a cold condition overnight, filtering, washing the sediments with water until the pH value becomes 5-6, drying, pulverizing the obtained dry extract and screening through 80-mesh sieve to give the extract of *Rhizoma Coptidis*.

Extracting twice by reflux the other seven crude drugs with water of 10 times the weight of the seven crude drugs for 1 hour per time; the combined extract liquid is concentrated into a concentrated extract liquid with a relative density of 1.03, cooling down, followed by adding 95% ethanol to make the ethanol content to 70%, standing still, filtering, recovering ethanol to give an extract with a relative density of 1.25, drying, pulverizing the obtained dry extract and screening through 80-mesh sieve.

Combining well the dry powder of extract obtained in the above three steps, adding lactose to prepare into capsules.

EXAMPLE 5

Formulation: 1200 g of *Radix Trichosanthis*, 900 g of *Radix Bupleuri*, 450 g of *Fructus Aurantii Immaturus*, 180 g of *Radix et Rhizoma Rhei*, 360 g of *Rhizoma Pinelliae*, 450 g of *Radix Scutellariae*, 360 g of *Rhizoma Coptidis*, 450 g of *Radix Paeoniae Alba* and 600 g of *Fructus Mume*.

The composition is prepared by the following method:

The above nine crude drugs are extracted twice by reflux with water of 10 times the weight of the crude drugs, 1.5 hour per time. The extract liquid is filtered, concentrated under reduced pressure into a concentrated extract liquid with the final volume (L) to the initial weight of the crude drugs (kg) in ratio of 1:1, anhydrous ethanol is added to make the content of ethanol to 75%. Obtained extract liquid is filtered and concentrated under reduced pressure into a dense extract.

EXAMPLE 6

Identical formulation with that of the Example 5 is provided.

The composition is prepared by the following method:

The following six crude drugs (*Radix Bupleuri, Radix Paeoniae Alba, Fructus Aurantii Immaturus, Radix et Rhizoma Rhei, Radix Scutellariae* and *Rhizoma Coptidis*) are extracted twice by reflux with 90% ethanol of 10 times the weight of the crude drugs for 1.5 hour per time to give the extract liquid (1) and the drug residue. The extract liquid (1) is filtered for further use.

Adding *Radix Trichosanthis, Fructus Mume* and *Rhizoma Pinelliae* into the drug residue, the extraction-by-reflux is performed twice with water of 10 times the total weight of the three crude drugs and the drug residue for 1.5 hour per time to give extract liquid (2). The extract liquid (2) is concentrated into a concentrated extract liquid with the final volume (L) to the initial weight of the crude drugs (kg) in ratio of 1:1. Anhydrous ethanol is added to make the content of ethanol to 75%, filtering for further use.

Combining the above extract liquid, and concentrating under reduced pressure into a dense extract.

EXAMPLE 7

Identical formulation with that of the Example 5 is provided.

The composition is prepared by the following method:

The above nine crude drugs are extracted twice by reflux with water, adding 49.5 kg water in each one-hour extraction; cooling down the extract liquid, filtering and combining. The combined filtrate is loaded onto 1.7 kg of AB-8 type macroporous adsorption resin in a speed of 6 times the column volume per hour. After washing with water of 6 times the column volume, the eluate is discarded. Then, the washing is conducted again with 95% ethanol of 5 times the column volume, and the ethanol eluate is combined. The ethanol is recovered from the combined ethanol eluate at 70° C. under reduced pressure to give an extract with a relative density of 1.35. Vacuum-dried is performed at 90° C. to obtain a dry extract, which is pulverized and screened through 80-mesh sieve. Starch is added into the screened dry powder to prepare into tablets.

EXAMPLE 8

Identical formulation with that of the Example 5 is provided.

The composition is prepared by the following method:

Extracting twice by reflux the *Radix Scutellariae* with water of 10 times the weight of the *Radix Scutellariae* for 1 hour per time; combining the extract liquid, adjusting pH value with concentrated hydrochloride acid to 1.5-2.0; the extract liquid is kept at 85° C. for 1 hour, standing still, filtering, washing the sediments with water until the pH value becomes 5-6, drying, pulverizing the obtained dry extract and screening through 80-mesh sieve to give the extract of *Radix Scutellariae*.

Extracting twice by reflux the *Rhizoma Coptidis* with 85% ethanol of 10 times the weight of the *Rhizoma Coptidis* for 2 hours per time; combining the extract liquid, filtering, recovering ethanol until no flavor of ethanol can be smelled, adjusting the pH value with concentrated hydrochloride acid to 1-2, storing under a cold condition overnight, filtering, washing the sediments with water until the pH value becomes 5-6, drying, pulverizing the obtained dry extract and screening through 80-mesh sieve to give the extract of *Rhizoma Coptidis*.

Extracting twice by reflux the other seven crude drugs with water of 10 times the weight of the seven crude drugs for 1 hour per time; the combined extract liquid is concentrated into a concentrated extract liquid with a relative density of 1.07, cooling down, followed by adding 95% ethanol to make the ethanol content to 70%, standing still, filtering, recovering ethanol to give an extract with a relative density of 1.35, drying, pulverizing the obtained dry extract and screening through 80-mesh sieve.

Combining well the dry powder of extract obtained in the above three steps, adding starch and preparing into tablets.

EXAMPLE 9

Formulation: 630 g of *Radix Trichosanthis*, 840 g of *Radix Bupleuri*, 630 g of *Fructus Aurantii Immaturus*, 210 g of *Radix et Rhizoma Rhei*, 420 g of *Rhizoma Pinelliae*, 630 g of *Radix Scutellariae*, 420 g of *Rhizoma Coptidis*, 630 g of *Radix Paeoniae Alba* and 630 g of *Fructus Mume*.

The composition is prepared by the following method:

The above nine crude drugs are extracted twice by reflux with water of 10 times the weight of the crude drugs, 1.5 hour per time. The extract liquid is filtered, concentrated under reduced pressure into a concentrated extract liquid with the final volume (L) to the initial weight of the crude drugs (kg) in ratio of 1:1, 95% ethanol is added to make the content of ethanol to 70%. Obtained extract liquid is filtered and concentrated under reduced pressure into a dense extract.

EXAMPLE 10

Identical formulation with that of the Example 9 is provided.

The composition is prepared by the following method:

The following six crude drugs (*Radix Bupleuri, Radix Paeoniae Alba, Fructus Aurantii Immaturus, Radix et Rhizoma Rhei, Radix Scutellariae* and *Rhizoma Coptidis*) are extracted twice by reflux with 80% ethanol 10 of times the weight of the crude drugs for 1.5 hour per time to give the extract liquid (1) and the drug residue. The extract liquid (1) is filtered for further use.

Adding *Radix Trichosanthis, Fructus Mume* and *Rhizoma Pinelliae* into the drug residue, the extraction-by-reflux is performed twice with water of 10 times the total weight of the three crude drugs and the drug residue for 1.5 hour per time to give extract liquid (2). The extract liquid (2) is concentrated into a concentrated extract liquid with the final volume (L) to the initial weight of the crude drugs (kg) in ratio of 1:1. 95% ethanol is added to make the content of ethanol to 70%, filtering for further use.

Combining the above extract liquid, and concentrating under reduced pressure into a dense extract.

EXAMPLE 11

Identical formulation with that of the Example 9 is provided.

The composition is prepared by the following method:

The above nine crude drugs are extracted twice by reflux with water, adding 50.4 kg water in each one-hour extraction; cooling down the extract liquid, filtering and combining. The combined filtrate is loaded onto 2.52 kg of AB-8 type macroporous adsorption resin in a speed of 5 times the column volume per hour. After washing with water of 5 times the column volume, the eluate is discarded. Then, the washing is conducted again with 90% ethanol of 3 times the column volume, and the ethanol eluate is combined. The ethanol is recovered from the combined ethanol eluate at 70° C. under reduced pressure to give an extract with a relative density of 1.30. Vacuum-dried is performed at 80° C. to obtain a dry extract, which is pulverized and screened through 80-mesh sieve. Microcrystalline cellulose is added into the screened dry powder to prepare into concentrated pills.

EXAMPLE 12

Identical formulation with that of the Example 9 is provided.

The composition is prepared by the following method:

Extracting twice by reflux the *Radix Scutellariae* with water of 10 times the weight of the *Radix Scutellariae* for 1 hour per time; combining the extract liquid, adjusting pH value with concentrated hydrochloride acid to 1.5-2.0; the extract liquid is kept at 80° C. for 1 hour, standing still, filtering, washing the sediments with water until the pH value becomes 5-6, drying, pulverizing the obtained dry extract and screening through 80-mesh sieve to give the extract of *Radix Scutellariae*.

Extracting twice by reflux the *Rhizoma Coptidis* with 75% ethanol of 10 times the weight of the *Rhizoma Coptidis* for 2 hours per time; combining the extract liquid, recovering ethanol until no flavor of ethanol can be smelled, adjusting the pH value with concentrated hydrochloride acid to 1-2, storing under a cold condition overnight, filtering, washing the sediments with water until the pH value becomes 5-6, drying, pulverizing the obtained dry extract and screening through 80-mesh sieve to give the extract of *Rhizoma Coptidis*.

Extracting twice by reflux the other seven crude drugs with water of 10 times the weight of the seven crude drugs for 1 hour per time; the combined extract liquid is concentrated into a concentrated extract liquid with a relative density of 1.05, cooling down, followed by adding 95% ethanol to make the ethanol content to 70%, standing still, filtering, recovering ethanol to give an extract with a relative density of 1.30, drying, pulverizing the obtained dry extract and screening through 80-mesh sieve.

Combining well the dry powder of extract obtained in the above three steps, adding microcrystalline cellulose to prepare into concentrated pills.

EXAMPLE 13

Formulation: 750 g of *Radix Trichosanthis*, 1500 g of *Radix Bupleuri*, 450 g of *Fructus Aurantii Immaturus*, 150 g of *Radix et Rhizoma Rhei*, 150 g of *Rhizoma Pinelliae*, 450 g of *Radix Scutellariae*, 150 g of *Rhizoma Coptidis*, 450 g of *Radix Paeoniae Alba*, 750 g of *Fructus Mume* and 450 g of *Fructus Crataegi*.

The composition is prepared by the following method:

The above ten crude drugs are extracted twice by reflux with water of 10 times the weight of the crude drugs, 1.5 hour per time. The extract liquid is filtered, concentrated under reduced pressure into a concentrated extract liquid with the final volume (L) to the initial weight of the crude drugs (kg) in ratio of 1:1, 90% ethanol is added to make the content of ethanol to 65%. Obtained extract liquid is filtered and concentrated under reduced pressure into a dense extract.

EXAMPLE 14

Identical formulation with that of the Example 13 is provided.

The composition is prepared by the following method:

The following six crude drugs (*Radix Bupleuri*, *Radix Paeoniae Alba*, *Fructus Aurantii Immaturus*, *Radix et Rhizoma Rhei*, *Radix Scutellariae* and *Rhizoma Coptidis*) are extracted twice by reflux with 75% ethanol of 10 times the weight of the crude drugs for 1.5 hour per time to give the extract liquid (1) and the drug residue. The extract liquid (1) is filtered for further use.

Adding *Radix Trichosanthis*, *Fructus Mume* and *Rhizoma Pinelliae* into the drug residue, the extraction-by-reflux is performed twice with water of 10 times the total weight of the four crude drugs and the drug residue for 1.5 hour per time to give extract liquid (2). The extract liquid (2) is concentrated into a concentrated extract liquid with the final volume (L) to the initial weight of the crude drugs (kg) in ratio of 1:1. 90% ethanol is added to make the content of ethanol to 65%, filtering for further use.

Combining the above extract liquid, and concentrating under reduced pressure into a dense extract.

EXAMPLE 15

Identical formulation with that of the Example 13 is provided.

The composition is prepared by the following method:

The above ten crude drugs are extracted twice by reflux with water, adding 52.5 kg water in each one-hour extraction; cooling down the extract liquid, filtering and combining. The combined filtrate is loaded onto 3.5 kg of AB-8 type macroporous adsorption resin in a speed of 4 times the column volume per hour. After washing with water of 4 times the column volume, the eluate is discarded. Then, the washing is conducted again with 80% ethanol of 2 times the column volume, and the ethanol eluate is combined. The ethanol is recovered from the combined ethanol eluate at 80° C. under reduced pressure to give an extract with a relative density of 1.35. Vacuum-dried is performed at 70° C. to obtain a dry extract, which is pulverized and screened through 80-mesh sieve. Lactose is added into the screened dry powder to prepare into capsules.

EXAMPLE 16

Identical formulation with that of the Example 13 is provided.

The composition is prepared by the following method:

Extracting twice by reflux the *Radix Scutellariae* with water of 10 times the weight of the *Radix Scutellariae* for 1 hour per time; combining the extract liquid, adjusting pH value with concentrated hydrochloride acid to 1.5-2.0; the extract liquid is kept at 75° C. for 1 hour, standing still, filtering, washing the sediments with water until the pH value becomes 5-6, drying, pulverizing the obtained dry extract and screening through 80-mesh sieve to give the extract of *Radix Scutellariae*.

Extracting twice by reflux the *Rhizoma Coptidis* with 70% ethanol of 10 times the weight of the *Rhizoma Coptidis* for 2 hours per time; combining the extract liquid, filtering, recovering ethanol until no flavor of ethanol can be smelled, adjusting the pH value with concentrated hydrochloride acid to 1-2, storing under a cold condition overnight, filtering, washing the sediments with water until the pH value becomes 5-6, drying, pulverizing the obtained dry extract and screening through 80-mesh sieve to give the extract of *Rhizoma Coptidis*.

Extracting twice by reflux the other eight crude drugs with water of 10 times the weight of the eight crude drugs for 1 hour per time; the combined extract liquid is concentrated into a concentrated extract liquid with a relative density of 1.07, cooling down, followed by adding 95% ethanol to make the ethanol content to 70%, standing still, filtering, recovering ethanol to give an extract with a relative density of 1.25, drying, pulverizing the obtained dry extract and screening through 80-mesh sieve.

Combining well the dry powder of extract obtained in the above three steps, adding lactose to prepare into capsules.

EXAMPLE 17

Formulation: 1200 g of *Radix Trichosanthis*, 900 g of *Radix Bupleuri*, 450 g of *Fructus Aurantii Immaturus*, 180 g of *Radix et Rhizoma Rhei*, 360 g of *Rhizoma Pinelliae*, 450 g of *Radix Scutellariae*, 360 g of *Rhizoma Coptidis*, 450 g of *Radix Paeoniae Alba*, 600 g of *Fructus Mume* and 450 g of *Fructus Crataegi*.

The composition is prepared by the following method:

The above ten crude drugs are extracted twice by reflux with water of 10 times the weight of the crude drugs, 1.5 hour per time. The extract liquid is filtered, concentrated under reduced pressure into a concentrated extract liquid with the final volume (L) to the initial weight of the crude drugs (kg) in ratio of 1:1, anhydrous ethanol is added to make the content of ethanol to 75%. Obtained extract liquid is filtered and concentrated under reduced pressure into a dense extract.

EXAMPLE 18

Identical formulation with that of the Example 17 is provided.

The composition is prepared by the following method:

The following six crude drugs (*Radix Bupleuri, Radix Paeoniae Alba, Fructus Aurantii Immaturus, Radix et Rhizoma Rhei, Radix Scutellariae* and *Rhizoma Coptidis*) are extracted twice by reflux with 90% ethanol of 10 times the weight of the crude drugs for 1.5 hour per time to give the extract liquid (1) and the drug residue. The extract liquid (1) is filtered for further use.

Adding *Radix Trichosanthis, Fructus Mume, Rhizoma Pinelliae* and *Fructus Crataegi* into the drug residue, the extraction-by-reflux is performed twice with water of 10 times the total weight of the four crude drugs and the drug residue for 1.5 hour per time to give extract liquid (2). The extract liquid (2) is concentrated into a concentrated extract liquid with the final volume (L) to the initial weight of the crude drugs (kg) in ratio of 1:1. Anhydrous ethanol is added to make the content of ethanol to 75%, filtering for further use.

Combining the above extract liquid, and concentrating under reduced pressure into a dense extract.

EXAMPLE 19

Identical formulation with that of the Example 17 is provided.

The composition is prepared by the following method:

The above ten crude drugs are extracted twice by reflux with water, adding 54 kg water in each one-hour extraction; cooling down the extract liquid, filtering and combining. The combined filtrate is loaded onto 1.8 kg of AB-8 type macroporous adsorption resin in a speed of 6 times the column volume per hour. After washing with water of 6 times the column volume, the eluate is discarded. Then, the washing is conducted again with 95% ethanol of 5 times the column volume, and the ethanol eluate is combined. The ethanol is recovered from the combined ethanol eluate at 70° C. under reduced pressure to give an extract with a relative density of 1.25. Vacuum-dried is performed at 90° C. to obtain a dry extract, which is pulverized and screened through 80-mesh sieve. Lactose is added into the screened dry powder to prepare into capsules.

EXAMPLE 20

Identical formulation with that of the Example 17 is provided.

The composition is prepared by the following method:

Extracting twice by reflux the *Radix Scutellariae* with water of 10 times the weight of the *Radix Scutellariae* for 1 hour per time; combining the extract liquid, adjusting pH value with concentrated hydrochloride acid to 1.5-2.0; the extract liquid is kept at 80° C. for 1 hour, standing still, filtering, washing the sediments with water until the pH value becomes 5-6, drying, pulverizing the obtained dry extract and screening through 80-mesh sieve to give the extract of *Radix Scutellariae*.

Extracting twice by reflux the *Rhizoma Coptidis* with 70% ethanol of 10 times the weight of the *Rhizoma Coptidis* for 2 hours per time; combining the extract liquid, filtering, recovering ethanol until no flavor of ethanol can be smelled, adjusting the pH value with concentrated hydrochloride acid to 1-2, storing under a cold condition overnight, filtering, washing the sediments with water until the pH value becomes 5-6, drying, pulverizing the obtained dry extract and screening through 80-mesh sieve to give the extract of *Rhizoma Coptidis*.

Extracting twice by reflux the other eight crude drugs with water of 10 times the weight of the eight crude drugs for 1 hour per time; the combined extract liquid is concentrated into a concentrated extract liquid with a relative density of 1.03, cooling down, followed by adding 95% ethanol to make the ethanol content to 70%, standing still, filtering, recovering ethanol to give an extract with a relative density of 1.35, drying, pulverizing the obtained dry extract and screening through 80-mesh sieve.

Combining well the dry powder of extract obtained in the above three steps, adding lactose to prepare into capsules.

EXAMPLE 21

Formulation: 833 g of *Radix Trichosanthis*, 667 g of *Radix Bupleuri*, 500 g of *Fructus Aurantii Immaturus*, 167 g of *Radix et Rhizoma Rhei*, 333 g of *Rhizoma Pinelliae*, 500 g of *Radix Scutellariae*, 333 g of *Rhizoma Coptidis*, 500 g of *Radix Paeoniae Alba*, 833 g of *Fructus Mume* and 500 g of *Fructus Crataegi*.

The composition is prepared by the following method:

The above ten crude drugs are extracted twice by reflux with water of 10 times the weight of the crude drugs, 1.5 hour per time. The extract liquid is filtered, concentrated under reduced pressure into a concentrated extract liquid with the final volume (L) to the initial weight of the crude drugs (kg) in ratio of 1:1, 95% ethanol is added to make the content of ethanol to 70%. Obtained extract liquid is filtered and concentrated under reduced pressure into a dense extract.

EXAMPLE 22

Identical formulation with that of the Example 21 is provided.

The composition is prepared by the following method:

The following six crude drugs (*Radix Bupleuri, Radix Paeoniae Alba, Fructus Aurantii Immaturus, Radix et Rhizoma Rhei, Radix Scutellariae* and *Rhizoma Coptidis*) are extracted twice by reflux with 80% ethanol of 10 times the weight of the crude drugs for 1.5 hour per time to give the extract liquid (1) and the drug residue. The extract liquid (1) is filtered for further use.

Adding *Radix Trichosanthis, Fructus Mume, Rhizoma Pinelliae* and *Fructus Crataegi* into the drug residue, the extraction-by-reflux is performed twice with water of 10 times the total weight of the four crude drugs and the drug residue for 1.5 hour per time to give extract liquid (2). The extract liquid (2) is concentrated into a concentrated extract liquid with the final volume (L) to the initial weight of the crude drugs (kg) in ratio of 1:1. 95% ethanol is added to make the content of ethanol to 70%, filtering for further use.

Combining the above extract liquid, and concentrating under reduced pressure into a dense extract.

EXAMPLE 23

Identical formulation with that of the Example 21 is provided.

The composition is prepared by the following method:

The above ten crude drugs are extracted twice by reflux with water, adding 51.7 kg water in each one-hour extraction;

cooling down the extract liquid, filtering and combining. The combined filtrate is loaded onto 2.6 kg of AB-8 type macroporous adsorption resin in a speed of 5 times the column volume per hour. After washing with water of 5 times the column volume, the eluate is discarded. Then, the washing is conducted again with 90% ethanol of 3 times the column volume, and the ethanol eluate is combined. The ethanol is recovered from the combined ethanol eluate at 70° C. under reduced pressure to give an extract with a relative density of 1.30. Vacuum-dried is performed at 80° C. to obtain a dry extract, which is pulverized and screened through 80-mesh sieve. Microcrystalline cellulose is added into the screened dry powder to prepare into concentrated pills.

EXAMPLE 24

Identical formulation with that of the Example 21 is provided.

The composition is prepared by the following method:

Extracting twice by reflux the *Radix Scutellariae* with water of 10 times the weight of the *Radix Scutellariae* for 1 hour per time; combining the extract liquid, adjusting pH value with concentrated hydrochloride acid to 1.5-2.0; the extract liquid is kept at 80° C. for 1 hour, standing still, filtering, washing the sediments with water until the pH value becomes 5-6, drying, pulverizing the obtained dry extract and screening through 80-mesh sieve to give the extract of *Radix Scutellariae*.

Extracting twice by reflux the *Rhizoma Coptidis* with 75% ethanol of 10 times the weight of the *Rhizoma Coptidis* for 2 hours per time; combining the extract liquid, filtering, recovering ethanol until no flavor of ethanol can be smelled, adjusting the pH value with concentrated hydrochloride acid to 1-2, storing under a cold condition overnight, filtering, washing the sediments with water until the pH value becomes 5-6, drying, pulverizing the obtained dry extract and screening through 80-mesh sieve to give the extract of *Rhizoma Coptidis*.

Extracting twice by reflux the other eight crude drugs with water of 10 times the weight of the eight crude drugs for 1 hour per time; the combined extract liquid is concentrated into a concentrated extract liquid with a relative density of 1.05, cooling down, followed by adding 95% ethanol to make the ethanol content to 70%, standing still, filtering, recovering ethanol to give an extract with a relative density of 1.30, drying, pulverizing the obtained dry extract and screening through 80-mesh sieve.

Combining well the dry powder of extract obtained in the above three steps, adding microcrystalline cellulose to prepare into concentrated pills.

EXAMPLE 25

Formulation: 500 g of *Radix Trichosanthis*, 750 g of *Radix Bupleuri*, 500 g of *Fructus Aurantii Immaturus*, 250 g of *Radix et Rhizoma Rhei*, 500 g of *Rhizoma Pinelliae*, 500 g of *Radix Scutellariae*, 500 g of *Rhizoma Coptidis*, 500 g of *Radix Paeoniae Alba*, 500 g of *Fructus Mume* and 500 g of *Fructus Crataegi*.

The composition is prepared by the following method:

The above ten crude drugs are extracted twice by reflux with water of 10 times the weight of the crude drugs, 1.5 hour per time. The extract liquid is filtered, concentrated under reduced pressure into a concentrated extract liquid with the final volume (L) to the initial weight of the crude drugs (kg) in ratio of 1:1, 95% ethanol is added to make the content of ethanol to 70%. Obtained extract liquid is filtered and concentrated under reduced pressure into a dense extract.

EXAMPLE 26

Identical formulation with that of the Example 25 is provided.

The composition is prepared by the following method:

The following six crude drugs (*Radix Bupleuri*, *Radix Paeoniae Alba*, *Fructus Aurantii Immaturus*, *Radix et Rhizoma Rhei*, *Radix Scutellariae* and *Rhizoma Coptidis*) are extracted twice by reflux with 80% ethanol of 10 times the weight of the crude drugs for 1.5 hour per time to give the extract liquid (1) and the drug residue. The extract liquid (1) is filtered for further use.

Adding *Radix Trichosanthis*, *Fructus Mume*, *Rhizoma Pinelliae* and *Fructus Crataegi* into the drug residue, the extraction-by-reflux is performed twice with water of 10 times the total weight of the four crude drugs and the drug residue for 1.5 hour per time to give extract liquid (2). The extract liquid (2) is concentrated into a concentrated extract liquid with the final volume (L) to the initial weight of the crude drugs (kg) in ratio of 1:1. 95% ethanol is added to make the content of ethanol to 70%, filtering for further use.

Combining the above extract liquid, and concentrating under reduced pressure into a dense extract.

EXAMPLE 27

Identical formulation with that of the Example 25 is provided.

The composition is prepared by the following method:

The above ten crude drugs are extracted twice by reflux with water, adding 50 kg water in each one-hour extraction; cooling down the extract liquid, filtering and combining. The combined filtrate is loaded onto 2.5 kg of AB-8 type macroporous adsorption resin in a speed of 4 times the column volume per hour. After washing with water of 5 times the column volume, the eluate is discarded. Then, the washing is conducted again with 92% ethanol of 4 times the column volume, and the ethanol eluate is combined. The ethanol is recovered from the combined ethanol eluate at 75° C. under reduced pressure to give an extract with a relative density of 1.25. Vacuum-dried is performed at 85° C. to obtain a dry extract, which is pulverized and screened through 80-mesh sieve. Dextrin is added into the screened dry powder to prepare into tablets.

EXAMPLE 28

Identical formulation with that of the Example 25 is provided.

The composition is prepared by the following method:

Extracting twice by reflux the *Radix Scutellariae* with water of 10 times the weight of the *Radix Scutellariae* for 1 hour per time; combining the extract liquid, adjusting pH value with concentrated hydrochloride acid to 1.5-2.0; the extract liquid is kept at 85° C. for 1 hour, standing still, filtering, washing the sediments with water until the pH value becomes 5-6, drying, pulverizing the obtained dry extract and screening through 80-mesh sieve to give the extract of *Radix Scutellariae*.

Extracting twice by reflux the *Rhizoma Coptidis* with 85% ethanol of 10 times the weight of the *Rhizoma Coptidis* for 2 hours per time; combining the extract liquid, filtering, recovering ethanol until no flavor of ethanol can be smelled, adjusting the pH value with concentrated hydrochloride acid to 1-2, storing under a cold condition overnight, filtering, washing the sediments with water until the pH value becomes 5-6, drying, pulverizing the obtained dry extract and screening through 80-mesh sieve to give the extract of *Rhizoma Coptidis*.

Extracting twice by reflux the other eight crude drugs with water of 10 times the weight of the eight crude drugs for 1 hour per time; the combined extract liquid is concentrated into a concentrated extract liquid with a relative density of 1.05, cooling down, followed by adding 95% ethanol to make the ethanol content to 70%, standing still, filtering, recovering ethanol to give an extract with a relative density of 1.25, drying, pulverizing the obtained dry extract and screening through 80-mesh sieve.

Combining well the dry powder of extract obtained in the above three steps, adding dextrin to prepare into tablets.

EXAMPLE 29

Formulation: 1200 g of *Radix Trichosanthis*, 800 g of *Radix Bupleuri*, 600 g of *Fructus Aurantii Immaturus*, 200 g of *Radix et Rhizoma Rhei*, 400 g of *Rhizoma Pinelliae*, 400 g of *Radix Scutellariae*, 200 g of *Rhizoma Coptidis*, 400 g of *Radix Paeoniae Alba*, 400 g of *Fructus Mume* and 400 g of *Fructus Crataegi*.

The composition is prepared by the following method:

The above ten crude drugs are extracted twice by reflux with water of 10 times the weight of the crude drugs, 1.5 hour per time. The extract liquid is filtered, concentrated under reduced pressure into a concentrated extract liquid with the final volume (L) to the initial weight of the crude drugs (kg) in ratio of 1:1, 90% ethanol is added to make the content of ethanol to 68%. Obtained extract liquid is filtered and concentrated under reduced pressure into a dense extract.

EXAMPLE 30

Identical formulation with that of the Example 29 is provided.

The composition is prepared by the following method:

The following six crude drugs (*Radix Bupleuri, Radix Paeoniae Alba, Fructus Aurantii Immaturus, Radix et Rhizoma Rhei, Radix Scutellariae* and *Rhizoma Coptidis*) are extracted twice by reflux with 85% ethanol of 10 times the weight of the crude drugs for 1.5 hour per time to give the extract liquid (1) and the drug residue. The extract liquid (1) is filtered for further use.

Adding *Radix Trichosanthis, Fructus Mume, Rhizoma Pinelliae* and *Fructus Crataegi* into the drug residue, the extraction-by-reflux is performed twice with water of 10 times the total weight of the four crude drugs and the drug residue for 1.5 hour per time to give extract liquid (2). The extract liquid (2) is concentrated into a concentrated extract liquid with the final volume (L) to the initial weight of the crude drugs (kg) in ratio of 1:1. 90% ethanol is added to make the content of ethanol to 68%, filtering for further use.

Combining the above extract liquid, and concentrating under reduced pressure into a dense extract.

EXAMPLE 31

Identical formulation with that of the Example 29 is provided.

The composition is prepared by the following method:

The above ten crude drugs are extracted twice by reflux with water, adding 50 kg water in each one-hour extraction; cooling down the extract liquid, filtering and combining. The combined filtrate is loaded onto 2.0 kg of AB-8 type macroporous adsorption resin in a speed of 6 times the column volume per hour. After washing with water of 4 times the column volume, the eluate is discarded. Then, the washing is conducted again with 92% ethanol of 3 times the column volume, and the ethanol eluate is combined. The ethanol is recovered from the combined ethanol eluate at 65° C. under reduced pressure to give an extract with a relative density of 1.30. Vacuum-dried is performed at 75° C. to obtain a dry extract, which is pulverized and screened through 80-mesh sieve. Lactose is added into the screened dry powder to prepare into capsules.

EXAMPLE 32

Identical formulation with that of the Example 29 is provided.

The composition is prepared by the following method:

Extracting twice by reflux the *Radix Scutellariae* with water of 10 times the weight of the *Radix Scutellariae* for 1 hour per time; combining the extract liquid, adjusting pH value with concentrated hydrochloride acid to 1.5-2.0; the extract liquid is kept at 75° C. for 1 hour, standing still, filtering, washing the sediments with water until the pH value becomes 5-6, drying, pulverizing the obtained dry extract and screening through 80-mesh sieve to give the extract of *Radix Scutellariae*.

Extracting twice by reflux the *Rhizoma Coptidis* with 75% ethanol of 10 times the weight of the *Rhizoma Coptidis* for 2 hours per time; combining the extract liquid, filtering, recovering ethanol until no flavor of ethanol can be smelled, adjusting the pH value with concentrated hydrochloride acid to 1-2, storing under a cold condition overnight, filtering, washing the sediments with water until the pH value becomes 5-6, drying, pulverizing the obtained dry extract and screening through 80-mesh sieve to give the extract of *Rhizoma Coptidis*.

Extracting twice by reflux the other eight crude drugs with water of 10 times the weight of the eight crude drugs for 1 hour per time; the combined extract liquid is concentrated into a concentrated extract liquid with a relative density of 1.05, cooling down, followed by adding 95% ethanol to make the ethanol content to 70%, standing still, filtering, recovering ethanol to give an extract with a relative density of 1.35, drying, pulverizing the obtained dry extract and screening through 80-mesh sieve.

Combining well the dry powder of extract obtained in the above three steps, adding lactose to prepare into capsules.

EXAMPLE 33

Formulation: 1000 g of *Radix Trichosanthis*, 600 g of *Radix Bupleuri*, 600 g of *Fructus Aurantii Immaturus*, 250 g of *Radix et Rhizoma Rhei*, 300 g of *Rhizoma Pinelliae*, 500 g of *Radix Scutellariae*, 300 g of *Rhizoma Coptidis*, 500 g of *Radix Paeoniae Alba*, 500 g of *Fructus Mume* and 300 g of *Fructus Crataegi*.

The composition is prepared by the following method:

The above ten crude drugs are extracted twice by reflux with water of 10 times the weight of the crude drugs, 1.5 hour per time. The extract liquid is filtered, concentrated under reduced pressure into a concentrated extract liquid with the final volume (L) to the initial weight of the crude drugs (kg) in ratio of 1:1, 99% ethanol is added to make the content of ethanol to 74%. Obtained extract liquid is filtered and concentrated under reduced pressure into a dense extract.

EXAMPLE 34

Identical formulation with that of the Example 33 is provided.

The composition is prepared by the following method:

The following six crude drugs (*Radix Bupleuri, Radix Paeoniae Alba, Fructus Aurantii Immaturus, Radix et Rhizoma Rhei, Radix Scutellariae* and *Rhizoma Coptidis*) are extracted twice by reflux with 90% ethanol of 10 times the weight of the crude drugs for 1.5 hour per time to give the extract liquid (1) and the drug residue. The extract liquid (1) is filtered for further use.

Adding *Radix Trichosanthis, Fructus Mume, Rhizoma Pinelliae* and *Fructus Crataegi* into the drug residue, the extraction-by-reflux is performed twice with water of 10 times the total weight of the four crude drugs and the drug residue for 1.5 hour per time to give extract liquid (2). The extract liquid (2) is concentrated into a concentrated extract liquid with the final volume (L) to the initial weight of the crude drugs (kg) in ratio of 1:1. 99% ethanol is added to make the content of ethanol to 74%, filtering for further use.

Combining the above extract liquid, and concentrating under reduced pressure into a dense extract.

EXAMPLE 35

Identical formulation with that of the Example 33 is provided.

The composition is prepared by the following method:

The above ten crude drugs are extracted twice by reflux with water, adding 48.5 kg water in each one-hour extraction; cooling down the extract liquid, filtering and combining. The combined filtrate is loaded onto 1.7 kg of AB-8 type macroporous adsorption resin in a speed of 5 times the column volume per hour. After washing with water of 4 times the column volume, the eluate is discarded. Then, the washing is conducted again with 85% ethanol of 5 times the column volume, and the ethanol eluate is combined. The ethanol is recovered from the combined ethanol eluate at 70° C. under reduced pressure to give an extract with a relative density of 1.35. Vacuum-dried is performed at 90° C. to obtain a dry extract, which is pulverized and screened through 80-mesh sieve. Lactose is added into the screened dry powder to prepare into capsules.

EXAMPLE 36

Identical formulation with that of the Example 33 is provided.

The composition is prepared by the following method:

Extracting twice by reflux the *Radix Scutellariae* with water of 10 times the weight of the *Radix Scutellariae* for 1 hour per time; combining the extract liquid, adjusting pH value with concentrated hydrochloride acid to 1.5-2.0; the extract liquid is kept at 80° C. for 1 hour, standing still, filtering, washing the sediments with water until the pH value becomes 5-6, drying, pulverizing the obtained dry extract and screening through 80-mesh sieve to give the extract of *Radix Scutellariae*.

Extracting twice by reflux the *Rhizoma Coptidis* with 80% ethanol of 10 times the weight of the *Rhizoma Coptidis* for 2 hours per time; combining the extract liquid, filtering, recovering ethanol until no flavor of ethanol can be smelled, adjusting the pH value with concentrated hydrochloride acid to 1-2, storing under a cold condition overnight, filtering, washing the sediments with water until the pH value becomes 5-6, drying, pulverizing the obtained dry extract and screening through 80-mesh sieve to give the extract of *Rhizoma Coptidis*.

Extracting twice by reflux the other eight crude drugs with water of 10 times the weight of the eight crude drugs for 1 hour per time; the combined extract liquid is concentrated into a concentrated extract liquid with a relative density of 1.05, cooling down, followed by adding 95% ethanol to make the ethanol content to 70%, standing still, filtering, recovering ethanol to give an extract with a relative density of 1.30, drying, pulverizing the obtained dry extract and screening through 80-mesh sieve.

Combining well the dry powder of extract obtained in the above three steps, adding lactose to prepare into capsules.

Experiment Example 1 Efficacy Test

1. Animals

Sixty of male SD rats with SPF grade, weighed 200-220 g.

2. Reagents, Drugs and Apparatus

Streptozotocin (STZ) was purchased from Sigma (USA) with batch number of 024K1211.

Anhydrous citric acid ($C_6H_8O_7 \cdot H_2O$) was purchased from Tianjin Chemical Reagent No. 1 Factory with batch number of 011121.

Sodium citrate ($Na_3C_6H_5O_7 \cdot 2H_2O$) was purchased from Tianjin Chemical Reagent No. 1 Factory with batch number of 011219.

Metformin (250 mg/tablet) was purchased from Tianjin Pacific Ocean Pharmaceutical Co., Ltd. with batch number of 040121.

Tested drugs (TL-1, TL-2 and TL-3) were powder of the extract respectively prepared by Examples 3, 8 and 9.

Stable blood glucose meter (One-Touch Ultra) was purchased from Lifescan Inc. (USA) with certificate number of 20032400735.

3. Preparation of Model Animals

SD rats were fasted overnight after one-week adaptation, intraperitoneal and injected a solution of 2% (W/V) STZ prepared with 0.1 mmol/L citric acid buffer solution (pH 4.4) (65 mg/kg). Three days later, the blood was sampled from tail vein to assay blood glucose. Those animals with blood glucose level equal to or higher than 16.7 mmol/L were considered to be successful model.

4. Administration Methods and Observation Index

The modeled rats were randomly divided into model group, Metformin (125 mg/kg) group and different treatment groups (corresponding to 15.5 g crude drugs/kg). After one-week adaptation and the blood glucose detection, rats were administered by gastric infusion, once a day. All of the drugs were diluted with physiological saline to prepare into suspension for administration. Animals were free to access of food and water during the 15-day testing period. At the seventh and fourteenth day after administration, the rats were fasted for two hours after administration. Respectively, blood was sampled from tail vein to assay blood glucose with blood glucose meter (one-touch ultra). At the same time, the body weights of the rats were measured.

5. Statistics

Results were expressed as mean±SD ($\bar{X} \pm SD$), and t-test was used to evaluate the significant difference of measurement data between two groups.

6. Results

As shown in Table 1, seven and fourteen days after administration, it is indicated that blood glucose level of STZ high-blood-glucose rats decreased significantly ($P<0.01$) in the different treatment groups at the dose of 15.5 g/kg.

TABLE 1

Comparison and change in the blood glucose level among groups

| | Dosage | Blood glucose level before administration (mmol/l) | blood glucose level, 7 days after administration (mmol/l) | Blood glucose level, 14 days after administration (mmol/l) |
|---|---|---|---|---|
| Control group | — | 5.99 ± 0.202 | 6.06 ± 0.165 | 6.01 ± 0.223 |
| Model group | — | 21.47 ± 2.351* | 22.35 ± 1.707* | 22.33 ± 1.614* |
| Metformin group | 125 mg/kg | 21.61 ± 2.066* | 18.64 ± 0.783*▲ | 17.54 ± 1.222*▲ |
| TL-1 | 15.5 g crude drugs/kg | 21.48 ± 1.686* | 18.13 ± 1.103*▲ | 17.21 ± 1.214*▲ |
| TL-2 | 15.5 g crude drugs/kg | 21.62 ± 1.734* | 17.97 ± 0.687*▲ | 17.04 ± 1.431*▲ |
| TL-3 | 15.5 g crude drugs/kg | 21.53 ± 1.752* | 17.32 ± 0.625*▲ | 17.02 ± 1.256*▲ |

($\bar{X}$ ± SD n = 10)
*Compared with the control group, p < 0.01;
▲Compared with the model group, p < 0.01.

What is claimed is:

1. A method for preparing a pharmaceutical composition for treatment of diabetes mellitus, wherein the pharmaceutical composition comprises extracts of the following crude drugs: 5-40 weight parts of *Radix Trichosanthis*, 10-30 weight parts of *Radix Bupleuri*, 3-15 weight parts of *Fructus Aurantii Immaturus*, 1-6 weight parts of *Radix et Rhizoma Rhei*, 1-12 weight parts of *Rhizoma Pinelliae*, 3-15 weight parts of *Radix Scutellariae*, 1-12 weight parts of *Rhizoma Coptidis*, 3-15 weight parts of *Radix Paeoniae Alba* and 5-20 weight parts of *Fructus Mume*, and optionally comprises pharmaceutically acceptable excipient; wherein the pharmaceutical composition is prepared by any one of the following four methods:

The first method comprising the following steps:
  providing the crude drugs in accordance with the weight parts as described above;
  extracting the crude drugs with water by reflux for at least one time to obtain at least one aqueous extract;
  collecting and filtering the at least one aqueous extract and concentrating under reduced pressure to obtain a concentrated extract;
  adding ethanol into the concentrated extract to make the ethanol content to 65-75%;
  filtering the concentrated extract to obtain a filtrate;
  concentrating the filtrate under reduced pressure to produce an extract; and
  optionally adding an excipient into the extract of the extract derived from concentrating the filtrate to prepare into a pharmaceutically acceptable dosage form;

The second method comprising the following steps:
  providing the crude drugs in accordance with weight parts as described above;
  extracting the crude drugs with water by reflux for at least one time to obtain at least one aqueous extract;
  collecting and cooling down the at least one aqueous extract, filtering to give a filtrate;
  loading the filtrate onto macro-porous adsorption resin, washing with water to obtain an eluate, and discarding the eluate;
  continuing to wash the resin with ethanol having a certain concentration for at least one time to obtain at least one ethanolic eluate;
  collecting the at least one ethanolic eluate and recovering ethanol under reduced pressure to give an extract; and
  optionally adding an excipient into the extract obtained in the previous step to prepare into a pharmaceutically acceptable dosage form;

The third method comprising the following steps:
  providing the crude drugs in accordance with weight parts as described above;
  extracting the following crude drugs with ethanol having a certain concentration by reflux to obtain an extraction residue and an ethanolic extract of: *Radix Bupleuri*, *Radix Paeoniae Alba*, *Fructus Aurantii Immaturus*, *Radix et Rhizoma Rhei*, *Radix Scutellariae* and *Rhizoma Coptidis*, separating the extraction residue and the ethanolic extract, and cooling down the ethanolic extract, filtering and combining the ethanolic extract to obtain a filtrate;
  adding the *Radix Trichosanthis*, the *Rhizoma pinelliae* and the *Fructus Mume* into the extraction residue from the extracting previous step to obtain a second extraction mixture, continuously extracting the second extraction mixture with water by reflux for at least one time to obtain at least one liquid extract, collecting and concentrating the at least one liquid extract under reduced pressure to obtain a concentrated liquid extract, followed by adding ethanol into the concentrated liquid extract to make the ethanol concentration 65-75% and filtering to obtain another filtrate;
  combining the filtrate and concentrating into an extract;
  optionally adding an excipient to the extract to prepare into a pharmaceutically acceptable dosage form;

The fourth method comprising the following steps:
  providing the crude drugs in accordance with weight parts as described above;
  extracting the *Radix Scutellariae* with water by reflux to obtain a liquid extract, combining the liquid extract, adjusting pH value to 1.5-2.0, keeping temperature, standing still, filtering the liquid extract to obtain sediments, washing the sediments with water until the pH value becomes 5-6, drying the sediments to give a dry powder extract of *Radix Scutellariae*;
  extracting the *Rhizoma Coptidis* with ethanol by reflux to obtain a liquid extract, combining the liquid extract, filtering the liquid extract, recovering ethanol until no odor of ethanol can be smelled, adjusting pH value to 1-2, storing the liquid extract under a cold condition overnight, filtering the liquid extract to obtain sediments, washing the sediments with water until the pH value becomes 5-6, drying the sediments to give a dry powder extract of *Rhizoma Coptidis*;
  extracting the *Radix Trichosanthis*, the *Radix Bupleuri*, the *Fructus Aurantii Immaturus*, the *Radix et Rhizoma Rhei*, the *Rhizoma Pinelliae*, the *Radix Paeoniae Alba* and the *Furctus Mume* with water by reflux for at least one time to obtain at least one liquid extract, collecting the at least one liquid extract, concentrating, cooling down, followed by adding 95% ethanol to make the ethanol content to 70%, standing still, filtering, recovering ethanol to give an extract, drying the extract to give a dry powder extract; and combining the dry powder extract obtained in the above three steps, into which an excipient is optionally added to prepare into a pharmaceutically acceptable dosage form.

2. The method according to claim 1, wherein that the weight parts of the crude drugs are as follows: 9 weight parts of *Radix Trichosanthis*, 12 weight parts of *Radix Bupleuri*, 9 weight parts of *Fructus Aurantii Immaturus*, 3 weight parts of *Radix et Rhizoma Rhei*, 6 weight parts of *Rhizoma Pinelliae*, 9 weight parts of *Radix Scutellariae*, 6 weight parts of *Rhizoma Coptidis*, 9 weight parts of *Radix Paeoniae Alba* and 9 weight parts of *Fructus Mume*.

3. The method according to claim 1, wherein that the crude drugs which are used to prepare the pharmaceutical composition further comprise *Fructus Crataegi*(Shanzha), and the weight parts of the crude drugs are as follows: 5-40 weight parts of *Radix Trichosanthis*, 10-30 weight parts of *Radix Bupleuri*, 3-15 weight parts of *Fructus Aurantii Immaturus*, 1-6 weight parts of *Radix et Rhizoma Rhei*, 1-12 weight parts of *Rhizoma Pinelliae*, 3-15 weight parts of *Radix Scutellariae*, 1-12 weight parts of *Rhizoma Coptidis*, 3-15 weight parts of *Radix Paeoniae Alba*, 5-20 weight parts of *Fructus Mume* and 3-15 weight parts of *Fructus Crataegi*.

4. The method according to claim 3, wherein that the weight parts of the crude drugs are as follows: 10-30 weight parts of *Radix Trichosanthis*, 10-30 weight parts of *Radix Bupleuri*, 3-15 weight parts of *Fructus Aurantii Immaturus*, 1-6 weight parts of *Radix et Rhizoma Rhei*, 1-12 weight parts of *Rhizoma Pinelliae*, 3-15 weight parts of *Radix Scutellariae*, 1-12 weight parts of *Rhizoma Coptidis*, 3-15 weight parts of *Radix Paeoniae Alba*, 5-20 weight parts of *Fructus Mume* and 3-15 weight parts of *Fructus Crataegi*.

5. The method according to claim 4, wherein that the weight parts of the crude drugs are as follows: 30 weight parts of *Radix Trichosanthis*, 12 weight parts of *Radix Bupleuri*, 9 weight parts of *Fructus Aurantii Immaturus*, 3 weight parts of *Radix et Rhizoma Rhei*, 6 weight parts of *Rhizoma Pinelliae*, 9 weight parts of *Radix Scutellariae*, 6 weight parts of *Rhizoma Coptidis*, 9 weight parts of *Radix Paeoniae Alba*, 15 weight parts of *Fructus Mume* and 9 weight parts of *Fructus Crataegi*, or the weight parts of the crude drugs are as follows: 15weight parts of *Radix Trichosanthis*, 12 weight parts of *Radix Bupleuri*, 9 weight parts of *Fructus Aurantii Immaturus*, 3 weight parts of *Radix et Rhizoma Rhei*, 6 weight parts of *Rhizoma Pinelliae*, 9 weight parts of *Radix Scutellariae*, 6 weight parts of *Rhizoma Coptidis*, 9 weight parts of *Radix Paeoniae Alba*, 15 weight parts of *Fructus Mume* and 9 weight parts of *Fructus Crataegi*.

6. The method according to claim 1, wherein, in the first method, the extraction-by-reflux is performed twice with water of 10 times (×10 fold) the weight of the crude drugs for 1.5 hour per time; the extract liquid is concentrated into a concentrated extract liquid with the final volume (L) to the initial weight of the crude drugs (kg) in ratio of 1:1; in the adding ethanol, the concentration of the added ethanol is 90-100%.

7. The method according to claim 6, wherein, in the adding of ethanol of the first method, the concentration of the added ethanol is 95%; after adding ethanol, the concentrated extract liquid contains 70% ethanol.

8. The method according to claim 1, wherein, in the second method, the extraction-by-reflux is performed twice with water of 10 times (×10 fold) the weight of the crude drugs for 1.0 hour per time.

9. The method according to claim 1, wherein, in the second method, the macro-porous resin is AB-8 type, the weight ratio of the resin to the crude drugs is 1:1.5-1:3.

10. The method according to claim 1, wherein, in the second method, in the loading of the filtrate, the extract liquid is loaded onto macro-porous adsorption resin in a speed of 4-6 times the column volume per hour; the amount of the washing water is 4-6 times the column volume; the concentration of ethanol for washing is 80-95%, preferably 90%; the volume of ethanol for washing is 2-5 times the column volume.

11. The method according to claim 1, wherein, in the second method, in the loading of the filtrate, the ethanol is recovered under reduced pressure at a temperature of 60-80° C.; and after recovering ethanol, the extract obtained has a relative density of 1.25-1.35.

12. The method according to claim 11, wherein the extract obtained has a relative density of 1.30.

13. The method according to claim 1, wherein, in the third method, in the extracting of the crude drugs, the extraction-by-reflux is performed twice with ethanol of 10times the crude drugs weight of the extracting the crude drugs for 1.5 hour per time; the concentration of ethanol is 75-90%, preferably 80%.

14. The method according to claim 1, wherein, in the third method, in the step of adding the *Radix Trichosanthis*, the *Rhizoma Pinelliae* and the *Fructus Mume*, the extracting by water with reflux is performed twice with water of 10 times the total weight of the *Radix Trichosanthis*, the *Rhizoma Pinelliae*, the *Fructus Mume* and the extraction residue for 1.5 hour per time; the extract liquid is concentrated into a concentrated extract liquid with the final volume (L) to the initial weight of the crude drugs (kg) in ratio of 1:1.

15. The method according to claim 1, wherein, in the third method, in the step of adding of the *Radix Trichosanthis*, the *Rhizoma Pinelliae* and the *Fructus Mume*, the concentration of the added ethanol is 90-100%, preferably 95%; after adding of ethanol, the concentrated extract liquid contains 70% ethanol.

16. The method according to claim 1, wherein, in the fourth method, in the extracting of the *Radix Scutellariae*, and the extraction-by-reflux is performed twice with water of 10 times the weight of the *Radix Scutellariae* for 1 hour per time; the extract liquid is kept at 75-85° C., preferably at 80° C.

17. The method according to claim 1, wherein, in the fourth method, in the extracting of the *Radix Scutellariae*, and the extraction-by-reflux is performed twice with ethanol of 10 times the weight of the *Rhizoma Coptidis* for 2 hours per time; the concentration of ethanol is 70-85%, preferably 75%.

18. The method according to claim 1, wherein, in the fourth method, in the extracting of the *Radix Scutellariae* and the *Rhizoma Coptidis*, and the pH is adjusted by concentrated hydrochloride acid.

19. The method according to claim 1, wherein, in the fourth method, in the step of extracting the *Radix Trichosanthis*, the *Radix Bupleuri*, the *Fructus Aurantii Immaturus*, the *Radix et Rhizoma Rhei*, the *Rhizoma Pinelliae*, the *Radix Paeoniae Alba*and the *Fructus Mume*, the extracting with water by reflux is performed twice with water of 10 times the weight of the *Radix Trichosanthis*, the *Radix Bupleuri*, the *Fructus Aurantii Immaturus*, the *Radix et Rhizoma Rhei*, the *Rhizoma Pinelliae*, the *Radix Paeoniae Alba* and the *Fructus Mume* for 1 hour per time; the combined extract liquid is concentrated into a concentrated extract liquid with a relative density of 1.03-1.07, preferably 1.05; after adding ethanol, recovering ethanol to give an extract with a relative density of 1.25-1.35, preferably 1.30.

20. The method of claim 1, wherein the *Radix Trichosanthis* is Tianhuafen, the *Radix Bupleuri* is Chaihu, the *Fructus Aurantii Immaturus* is Zhishi, the *Radix et Rhizoma Rhei* is Dahuang, the *Rhizoma Pinelliae* is Banxia, the *Radix Scutellariae* is Huangqin, the *Rhizoma Coptidis* is Huanglian, the *Radix Paeoniae Alba* is Baishao and the *Fructus Mume* is Wumei.

21. A method for preparing a pharmaceutical composition for treatment of diabetes mellitus, wherein the pharmaceutical composition comprises extracts of the following crude drugs: 5-40 weight parts of *Radix Trichosanthis* (Tianhuafen), 10-30 weight parts of *Radix Bupleuri* (Chaihu), 3-15 weight parts of *Fructus Aurantii Immaturus* (Zhishi), 1-6 weight parts of *Radix et Rhizoma Rhei* (Dahuang), 1-12 weight parts of *Rhizoma Pinelliae* (Banxia), 3-15 weight parts of *Radix Scutellariae* (Huangqin), 1-12 weight parts of *Rhizoma Coptidis* (Huanglian), 3-15weight parts of *Radix Paeoniae Alba* (Baishao) and 5-20 weight parts of *Fructus Mume*(Wumei), and optionally comprises pharmaceutically acceptable excipient; the method comprising:
    providing the crude drugs in accordance with the weight parts as described above;
    extracting the crude drugs with water by reflux for at least one time to obtain at least one aqueous extract;
    collecting and filtering the at least one aqueous extract and concentrating under reduced pressure to obtain a concentrated extract;
    adding ethanol into the concentrated extract to make the ethanol content to 65-75%;
    filtering the concentrated extract to obtain a filtrate;
    concentrating the filtrate under reduced pressure to produce an extract; and
    optionally adding an excipient into the extract of the extract derived from concentrating the filtrate to prepare into a pharmaceutically acceptable dosage form.

22. A method for preparing a pharmaceutical composition for treatment of diabetes mellitus, wherein the pharmaceutical composition comprises extracts of the following crude drugs: 5-40 weight parts of *Radix Trichosanthis* (Tianhuafen), 10-30 weight parts of *Radix Bupleuri* (Chaihu), 3-15 weight parts of *Fructus Aurantii Immaturus* (Zhishi), 1-6 weight parts of *Radix et Rhizoma Rhei* (Dahuang), 1-12 weight parts of *Rhizoma Pinelliae* (Banxia), 3-15 weight parts of *Radix Scutellariae* (Huangqin), 1-12 weight parts of *Rhizoma Coptidis* (Huanglian), 3-15weight parts of *Radix Paeoniae Alba* (Baishao) and 5-20 weight parts of *Fructus Mume*(Wumei), and optionally comprises pharmaceutically acceptable excipient; the method comprising:
    providing the crude drugs in accordance with weight parts as described above;
    extracting the crude drugs with water by reflux for at least one time to obtain at least one aqueous extract;
    collecting and cooling down the at least one aqueous extract, filtering to give a filtrate;
    loading the filtrate onto macro-porous adsorption resin, washing with water to obtain an eluate, and discarding the eluate;
    continuing to wash the resin with ethanol having a certain concentration for at least one time to obtain at least one ethanolic eluate;
    collecting the at least one ethanolic eluate and recovering ethanol under reduced pressure to give an extract; and
    optionally adding an excipient into the extract obtained in the previous step to prepare into a pharmaceutically acceptable dosage form.

23. A method for preparing a pharmaceutical composition for treatment of diabetes mellitus, wherein the pharmaceutical composition comprises extracts of the following crude drugs: 5-40 weight parts of *Radix Trichosanthis* (Tianhuafen), 10-30 weight parts of *Radix Bupleuri* (Chaihu), 3-15 weight parts of *Fructus Aurantii Immaturus* (Zhishi), 1-6 weight parts of *Radix et Rhizoma Rhei* (Dahuang), 1-12 weight parts of *Rhizoma Pinelliae* (Banxia), 3-15 weight parts of *Radix Scutellariae* (Huangqin), 1-12 weight parts of *Rhizoma Coptidis* (Huanglian), 3-15 weight parts of *Radix Paeoniae Alba* (Baishao) and 5-20 weight parts of *Fructus Mume*(Wumei), and optionally comprises pharmaceutically acceptable excipient; the method comprising:
    providing the crude drugs in accordance with weight parts as described above;
    extracting the following crude drugs with ethanol having a certain concentration by reflux to obtain an extraction residue and an ethanolic extract of: *Radix Bupleuri, Radix Paeoniae Alba, Fructus Aurantii Immaturus, Radix et Rhizoma Rhei, Radix Scutellariae* and *Rhizoma Coptidis*, separating the extraction residue and the ethanolic extract, and cooling down the ethanolic extract, filtering and combining the ethanolic extract to obtain a filtrate;
    adding the *Radix Trichosanthis*, the *Rhizoma pinelliae* and the *Fructus Mume* into the extraction residue from the extracting previous step to obtain a second extraction mixture, continuously extracting the second extraction mixture with water by reflux for at least one time to obtain at least one liquid extract, collecting and concentrating the at least one liquid extract under reduced pressure to obtain a concentrated liquid extract, followed by adding ethanol into the concentrated liquid extract to make the ethanol concentration 65-75% and filtering to obtain another filtrate;
    combining the filtrate and the another filtrate and concentrating into an extract;
    optionally adding an excipient to the extract to prepare into a pharmaceutically acceptable dosage form.

24. A method for preparing a pharmaceutical composition for treatment of diabetes mellitus, wherein the pharmaceutical composition comprises extracts of the following crude drugs: 5-40 weight parts of *Radix Trichosanthis* (Tianhuafen), 10-30 weight parts of *RadixBupleuri* (Chaihu), 3-15 weight parts of *Fructus Aurantii Immaturus* (Zhishi), 1-6 weight parts of *Radix et Rhizoma Rhei* (Dahuang), 1-12 weight parts of *Rhizoma Pinelliae* (Banxia), 3-15 weight parts of *Radix Scutellariae* (Huangqin), 1-12 weight parts of *Rhizoma Coptidis* (Huanglian), 3-15 weight parts of *Radix Paeoniae Alba* (Baishao) and 5-20 weight parts of *Fructus Mume*(Wumei), and optionally comprises pharmaceutically acceptable excipient; the method comprising:
    providing the crude drugs in accordance with weight parts as described above;
    extracting the *Radix Scutellariae* with water by reflux to obtain a liquid extract, combining the liquid extract, adjusting pH value to 1.5-2.0, keeping temperature, standing still, filtering the liquid extract to obtain sediments, washing the sediments with water until the pH value becomes 5-6, drying the sediments to give a dry powder extract of *Radix Scutellariae*;
    extracting the *Rhizoma Coptidis* with ethanol by reflux to obtain a liquid extract, combining the liquid extract, filtering the liquid extract, recovering ethanol until no odor of ethanol can be smelled, adjusting pH value to 1-2, storing the liquid extract under a cold condition overnight, filtering the liquid extract to obtain sediments, washing the sediments with water until the pH value becomes 5-6, drying the sediments to give a dry powder extract of *Rhizoma Coptidis;* extracting the *Radix Trichosanthis*, the *Radix Bupleuri*, the *Fructus Aurantii Immaturus*, the *Radix et Rhizoma Rhei*, the *Rhizoma Pinelliae*, the *Radix Paeoniae Alba* and the *Furctus Mume* with water by reflux for at least one time to obtain at least one liquid extract, collecting the at least one liquid extract, concentrating, cooling down, followed by adding 95% ethanol to make the ethanol content to 70%, standing still, filtering, recovering ethanol to give an extract, drying the extract to give a dry powder extract; and combining the dry powder extract obtained in the above three steps, into which an excipient is optionally added to prepare into a pharmaceutically acceptable dosage form.

25. A pharmaceutical composition prepared by the method according to claim 1.

26. The pharmaceutical composition according to claim 25, wherein the pharmaceutical composition is a pharmaceutically acceptable dosage form thereof.

\* \* \* \* \*